United States Patent [19]

Goto et al.

[11] Patent Number: 4,935,506

[45] Date of Patent: Jun. 19, 1990

[54] 3-PHENYLTHIOSIALIC ACID DERIVATIVE, SIALIC ACID-CONTAINING OLIGOSACCHARIDE DERIVATIVE AND PROCESS FOR PREPARING THESE COMPOUNDS

[75] Inventors: Toshio Goto; Tadao Kondo, both of Nagoya, Japan

[73] Assignee: MECT Corporation, Tokyo, Japan

[21] Appl. No.: 365,980

[22] Filed: Jun. 12, 1989

[30] Foreign Application Priority Data

Jun. 16, 1988 [JP] Japan .................................. 63-149136
Sep. 24, 1988 [JP] Japan .................................. 63-239479

[51] Int. Cl.$^5$ ...................... C07G 3/00; C07G 17/00; C07H 5/00; C07H 11/00
[52] U.S. Cl. .................................... 536/4.1; 536/18.7; 536/22; 536/54; 536/118; 536/122; 536/124; 536/17.2

[58] Field of Search .................. 536/4.1, 1.1, 17.2, 536/17.9, 18.7, 22, 54, 118, 124, 121, 122

[56] References Cited

U.S. PATENT DOCUMENTS 4,691,012 9/1987 Ogura et al. ........................... 536/23
4,694,076 9/1987 Ogawa et al. ......................... 536/4.1

*Primary Examiner*—Ronald W. Griffin
*Assistant Examiner*—Everett White
*Attorney, Agent, or Firm*—Rodman & Rodman

[57] ABSTRACT

Sialic acid derivatives and process for preparing these compounds. In these compounds, a phenylthio group is stereo-selectively incorporated at the 3-position of the sialic acid. These compounds are useful as intermediates for synthesizing various glycosides such as ganglioside, a blood type determining factor, $GQ_{1b}$ etc. The present invention also relates to sialic acid-containing oligosaccharide derivatives and process for preparing them.

7 Claims, No Drawings

3-PHENYLTHIOSIALIC ACID DERIVATIVE, SIALIC ACID-CONTAINING OLIGOSACCHARIDE DERIVATIVE AND PROCESS FOR PREPARING THESE COMPOUNDS

BACKGROUND OF THE INVENTION (1) Field of the Invention

This invention relates to a sialic acid derivative which is available for synthesis of a glycoside and a process for preparing the same.

(2) Related Art Statement

A sialic acid represented by N-acetylneuraminic acid (NANA) has widely been distributed in various glycosides such as ganglioside, a blood type determining factor, $GQ_{lb}$, etc. in a biological field, and it has been known that it pertains largely to development of physiological activity of saccharide chain. Accordingly, in order to elucidate the function thereof, it has been deemed to be important to synthesize a sialic acid derivative.

SUMMARY OF THE INVENTION

An object of the present invention is to provide a sialic acid derivative in which a phenylthio group is stereoselectively incorporated at the 3-position of the sialic acid.

Another object of the present invention is to provide a process for preparing a sialic acid derivative in which a phenylthio group is stereoselectively incorporated at the 3-position of the sialic acid.

A further object of the present invention is to provide a sialic acid-containing oligosaccharide derivative.

A further object of the present invention is to provide a process for preparing a sialic acid-containing oligosaccharide derivative using a sialic acid derivative in which a phenylthio group is stereoselectively incorporated at the 3-position of the sialic acid.

The above and the other objects of the present invention and characteristics will be more clarified by the following detailed description and Examples.

DETAILED DESCRIPTION OF THE PREFERRED EMBODIMENTS

The 3-phenylthiosialic acid derivative of the present invention is a compound represented by the following formula (Ia) or (Ib):

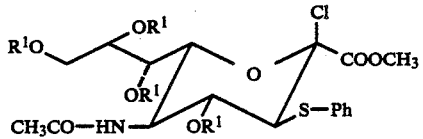

(Ia)

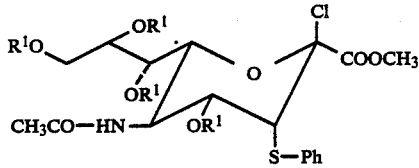

(Ib)

wherein $R^1$ represents an acetyl group, a benzyl group or a benzoyl group, and Ph represents a phenyl group, hereinafter the same.

The other 3-phenylthiosialic acid derivative of the present invention is a compound wherein $R^1$ at the 8-position or 9-position of the compound represented by the above formula (Ia) or (Ib) is replaced with:

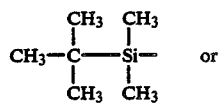

or

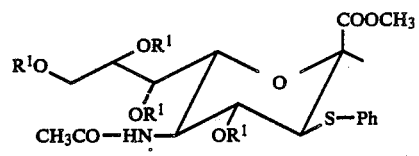

These 3-phenylthiosialic acid derivatives are very useful compounds, for example, as intermediates for synthesizing various glycosides such as ganglioside, a blood type determining factor, $GQ_{lb}$ etc.

The above 3-phenylthiosialic acid derivative can be prepared with a one step reaction and good yield by reacting the compound represented by the formula (II):

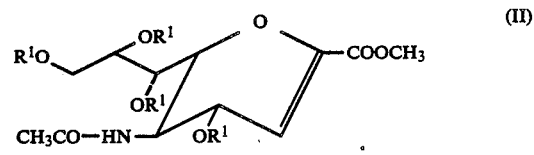

(II)

with a phenylsulfenyl chloride in a polar solvent.

The sialic acid-containing oligosaccharide derivative of the present invention is a compound represented by the formula (III):

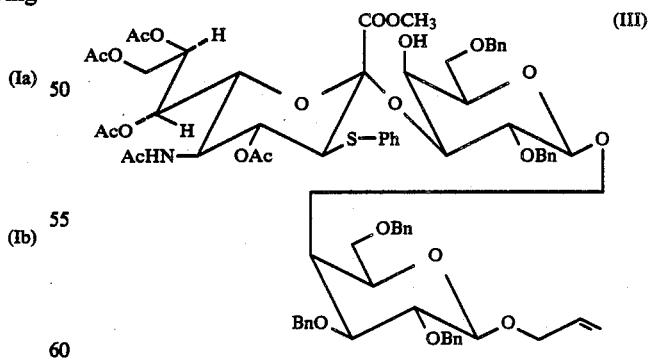

(III)

wherein Ac represents an acetyl group and Bn represents a benzyl group, hereinafter the same.

The other sialic acid-containing oligosaccharide derivative of the present invention is a compound represented by the formula (IV):

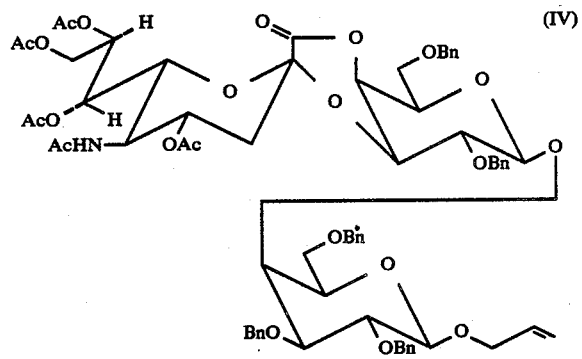

The sialic acid-containing oligosaccharide derivative represented by the above formula (IV) can be prepared by, firstly obtaining the compound represented by the above formula (III) by reacting a dichloroethane mixed solution containing the 3-phenylthiosialic acid derivative represented by the formula (Ia), the compound represented by the formula (V):

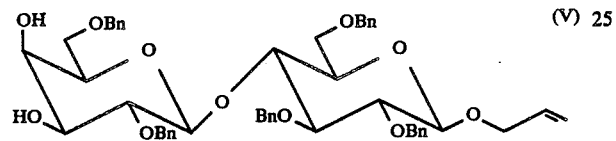

molecular sieves and Na$_2$HPO$_4$ with a toluene solution containing silver trifluoroacetate, and then reacting the compound represented by the formula (III) with a toluene mixed solution containing α'-azobis-isobutyronitrile, and with (n-C$_4$H$_9$)$_3$SnH.

In the following examples, the process for preparing the 3-phenylthiosialic acid derivative represented by the formula (Ia) or (Ib), and the sialic acid-containing oligosaccharide derivative represented by the formula (III) or (IV) will be explained.

EXAMPLE 1

To a solution of 10 g (2.1 mmole) of 2-dehydroxy-3-dehydro NANA represented by the following formula (II):

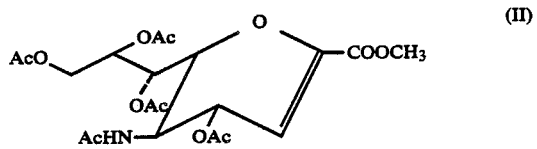

dissolved in 9 ml of CH$_2$Cl$_2$ was added dropwise 0.7 g of phenylsulfenyl chloride prepared immediately before at 30° C. under stirring, and then the reaction mixture was allowed to stand in a dark place for 2 days. Then, this reaction mixture was washed successively with a 5% NaHCO$_3$ aqueous solution, H$_2$O and a saturated saline solution, dried over Na$_2$SO$_4$ and the solvent was distilled off under reduced pressure. The residue was applied to a silica gel chromatography to give two kinds of adduct products represented by the following formulae (Ia) (S-Ph: equatorial, Yield=77%) and (Ib) (S-Ph: axial, Yield=15%, amorphous).

(1) Methyl 5-acetamido-4,7,8,9-tetra-O-acetyl-2-chloro-3-phenylthio-2,3,5-tri-O-deoxy-D-erythro-L-gluco-2-noneuropyranosonate

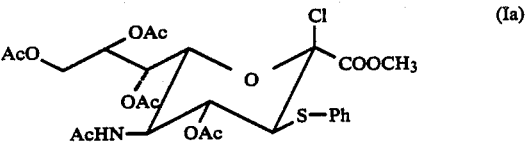

$^1$H-NMR δ (CDCl$_3$): 1.87, 1.90, 2.05, 2.11, 2.12 (3H, each s, CH$_3$CO), 3.82 (3H, s, CH$_3$OCO), 3.99 (1H, dd, J=5.0, 12.5 Hz, H-9), 4.00 (1H, d, J=11 Hz, H-3), 4.27 (1H, dd, J=2.5, 12.5 Hz, H-9), 4.34 (1H, q, J=10 Hz, H-5), 4.40 (1H, dd, J=2.5, 10 Hz, H-6), 5.12 (1H, ddd, J=2.5, 5.0, 8.0 Hz, H-8), 5.36 (1H, d, J=10, 11 Hz, H-4), 5.43 (1H, dd, J=2.5, 8 Hz, H-7), 5.44 (1H, d, J=10 Hz, NHCOCH$_3$, exchangeable), 7.2–7.5 (5H, aromatic).

(2) Methyl 5-acetamido-4,7,8,9-tetra-O-acetyl-2-chloro-3-phenylthio-2,3,5-trideoxy-D-erythro-L-manno-2-noneuropyranosonate

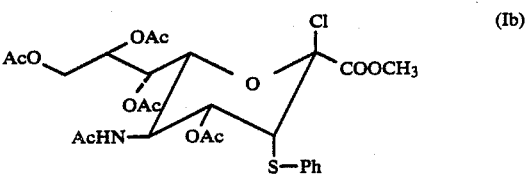

$^1$H-NMR δ (CDCl$_3$): 1.81, 1.95, 2.06, 2.07, 2.20 (3H, each s, CH$_3$CO), 3.85 (3H, s, CH$_3$CO), 4.16 (1H, dd, J=6, 12.5 Hz, H-9), 4.18 (1H, d, J=4 Hz, H-3), 4.44 (1H, dd, J=2, 11 Hz, H-6), 4.49 (1H, dd, J=2.5, 12.5 Hz, H-9), 4.54 (1H, br. q, J=9.5, 10.5 Hz, H-5), 5.27 (1H, ddd, J=2.0, 2.5, 7.0 Hz, H-8), 5.45 (1H, d, J=9.5 Hz, NHCOCH$_3$, exchangeable), 5.85 (1H, dd, J=4, 10.5 Hz, H-4), 7.2–7.6 (5H, aromatic).

In the above synthesis reaction, yields of the products when using a solvent other than CH$_2$Cl$_2$ are shown in Table 1.

TABLE 1

| Solvent | Reaction temperature (°C.) | Yield (%) (Ia) | Yield (%) (Ib) |
|---|---|---|---|
| Toluene | 80 | 46 | 5 |
| Acetonitrile | 30 | 35 | 60 |
| Nitromethane | 30 | 30 | 64 |
| Tetrahydrofuran | 30 | No addition reaction | |
| Ether | 30 | No addition reaction | |
| Dimethylsulfoxide | 30 | No addition reaction | |

EXAMPLE 2

(1) To a mixed liquor of 100 mg (0.16 mmole) of the compound (formula (Ia)) obtained in the above Example 1, 270 mg (0.32 mmole) of the compound represented by the formula (V):

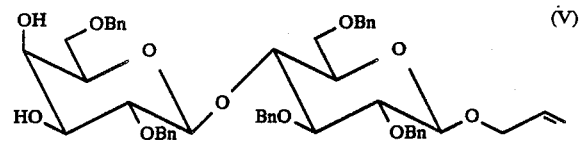

(wherein Bn represents a benzyl group), 300 mg of molecular sieves and 45 mg of Na₂HPO₄ in 2 ml of dichloroethane, was added dropwise a solution of 82 mg (0.32 mmole) of trifluoroacetic acid dissolved in 1 ml of toluene, and the mixture was stirred at dark place (at 70° C.) for 3.5 hours, filtered through Celite, and the filtrate was washed sufficiently with ethyl acetate. Then, this reaction mixture was washed successively with a Na₂S₂O₃ aqueous solution, a NaHCO₃ aqueous solution, H₂O and a saturated saline solution, passed through an anhydrous Na₂SO₄ column, and then condensed to dryness. Next, the residue was applied to a column chromatography to give 48 mg (Yield: 21%) of amorphous powder of the compound represented by the following formula (III).

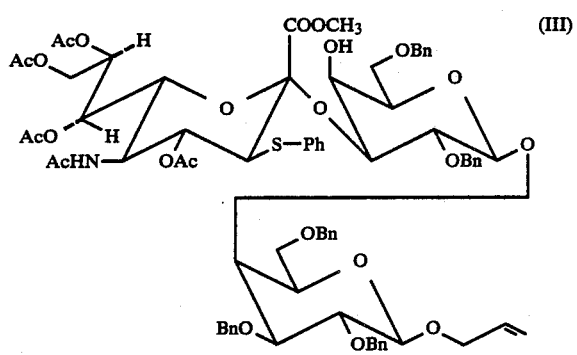

¹H-NMR δ (CDCl₃), 500 MHz: 1.88, 1.92, 1.95, 1.96, 2.04 (3H, each, s, CH₃CO), 2.63 (1H, br, HO), 3.31 (1H, ddd, J=1, 5, 10 Hz, H-5'), 3.34 (1H, d, J=11 Hz, H-3), 3.41 (1H, t, J=8 Hz, H-2'), 3.43 (1H, t, J=9 Hz, H-2''), 3.46–3.60 (2H, m), 3.54 (1H, t, J=9 Hz, H-3'), 3.70 (1H, dd, J=5, 11 Hz, H-6'), 3.71 (1H, dd, J=6, 8 Hz), 3.77 (1H, dd, J=1, 11 Hz, H-6''), 3.83 (1H, s, CH₃O), 3.89 (1H, d, J=3 Hz, H-4''), 3.93 (1H, t, J=9 Hz, H-4'), 3.96 (1H, dd, J=6, 13 Hz, H-9), 4.12 (1H, dd, J=2, 11 Hz, H-6), 4.26 (1H, q, J=11 Hz, H-5), 4.30 (1H, dd, J=3, 13 Hz, H-9), 4.34 (1H, dd, J=3, 10 Hz, H-3''), 4.34 (1H, d, J=12 Hz, CH₂Ph), 4.39 (1H, d, J=8 Hz, H-1'), 4.45 (1H, d, J=12 Hz, CH₂Ph), 4.47 (1H, d, J=12 Hz, CH₂Ph), 4.50 (1H, d, J=12 Hz, CH₂Ph), 4.55 (1H, d, J=8 Hz, H-1''), 4.56 (1H, d, J=13 Hz, CH₂Ph), 4.60 (1H, d, J=13 Hz, CH₂Ph), 4.70 (1H, d, J=11 Hz, CH₂Ph), 4.74 (1H, d, J=11 Hz, CH₂Ph), 4.89 (1H, d, J=11 Hz, CH₂Ph), 4.98 (1H, d, J=11 Hz, CH₂Ph), 5.28 (1H, t, J=11 Hz, H-4), 5.30 (1H, dd, J=2, 8 Hz, H7), 5.32 (1H, d, J=11 Hz, NH), 5.38 (1H, ddd, J=3, 6, 8 Hz, H-8), 7.16–7.52 (30H, aromatic), O-allyl, 4.07–4.13 (1H, m), at the neighbor of 4.37 (1H, m), 5.18 (1H, m), 5.94–6.00 (2H, m).

(2) To a mixed liquor of 13 mg of the compound represented by the formula (III) obtained in the above (1) and 3 mg of α-azobis-isobutyronitrile in 0.5 ml of toluene, was added dropwise (n-C₄H₉)₃SnH, and the reaction mixture was stirred for one hour and then condensed to dryness. The residue was separated and collected by TLC to obtain colorless oily substance of the compound represented by the following formula (IV).

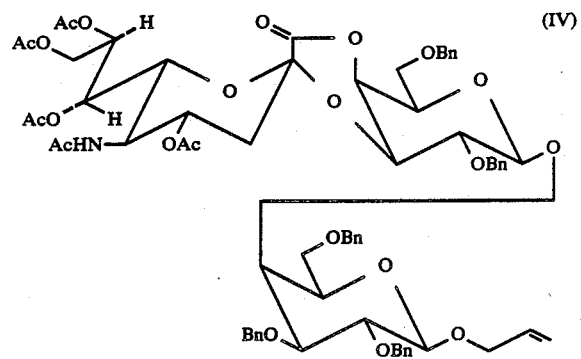

¹H-NMR δ (CDCl₃), 500 MHz: 1.85 (1H, t, J=12 Hz, H-3), 1.88, 1.94, 2.01, 2.05, 2.15 (3H, each, s, CH₃CO), 3.25 (1H, ddd, J=8, 9 Hz, H-2''), 3.37 (1H, ddd, J=1, 4, 10 Hz, H-5'), 3.41 (1H, t, J=9 Hz, H-2'), 3.43 (1H, dd, J=10, 19 Hz, ?), 3.55 (1H, t, J=10 Hz, H-3'), 3.70 (1H, dd, J=1, 2 Hz, H-6'), 3.71 (1H, dd, J=2, 10 Hz, H-6), 3.76 (1H, dd, J=5, 11 Hz, ?), 3.78 (1H, dd, J=4, 11 Hz, H-6'), 3.90 (1H, dd, J=7, 13 Hz, H-9), 3.97 (1H, t, J=10 Hz, H-4'), 4.07 (1H, dd, J=4, 10 Hz, H-3''), 4.13 (1H, dd, J=5, 13 Hz, ?), 4.19 (1H, q, J=10 Hz, H-5), 4.28 (1H, d, J=13 Hz, CH₂Ph), 4.35–4.50 (m), 4.57 (1H, d, J=13 Hz, CH₂Ph), 4.62 (1H, d, J=11 Hz, CH₂Ph), 4.67 (1H, d, J=11 Hz, CH₂Ph), 4.72 (1H, d, J=11 Hz, CH₂Ph), 4.76 (1H, d, J=11 Hz, CH₂Ph), 4.87 (1H, d, J=4 Hz, H-4''), 4.90 (1H, d, J=11 Hz, CH₂Ph), 4.91 (1H, d, J=11 Hz, CH₂Ph), 5.05 (1H, d, J=3 Hz, t, J=6 Hz, H-8), 5.25 (1H, dd, J=2, 6 Hz, H-7), 5.27 (1H, d, J=11 Hz, NH), 5.50 (1H, d, J=5 Hz, t, J=11 Hz, H-4), 7.2–7.5 (25H, m, aromatic), O-allyl, at the neighbor of 4.4 (1H), 5.20 (1H), 5.33 (1H), 5.9–6.0 (2H).

What is claimed is:
1. A 3-phenylthiosialic acid derivative represented by the formula (Ia) or (Ib):

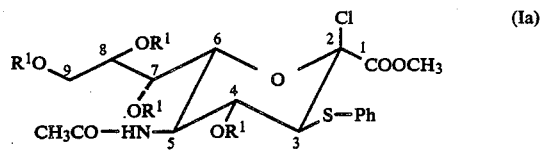

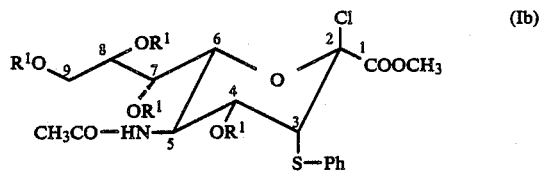

wherein R¹ represents an acetyl group, a benzyl group or a benzoyl group; and Ph represents a phenyl group.

2. A 3-phenylthiosialic acid derivative according to claim 1, wherein at least one of R¹s at the 8-position and 9-position of said 3-phenylthiosialic acid is replaced with

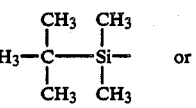

or

-continued

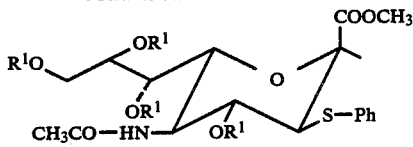

wherein R[1] and Ph have the same meanings as defined above.

3. A process for preparing the 3-phenylthiosialic acid derivative according to claim 1, which comprises reacting the compound represented by the formula (II):

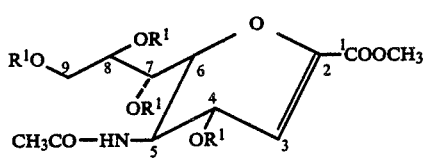

wherein R[1] represents an acetyl group, a benzyl group or a benzoyl group,
with phenylsulfenyl chloride in a polar solvent.

4. A process for preparing the 3-phenylthiosialic acid according to claim 3, wherein at least one of R[1]s at the 8-position and 9-position of the compound represented by the formula (II) is replaced with

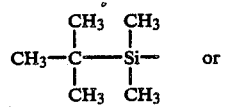 or

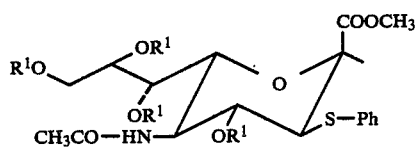

wherein R[1] and Ph have the same meanings as defined above.

5. A sialic acid-containing oligosaccharide derivative represented by the formula (III):

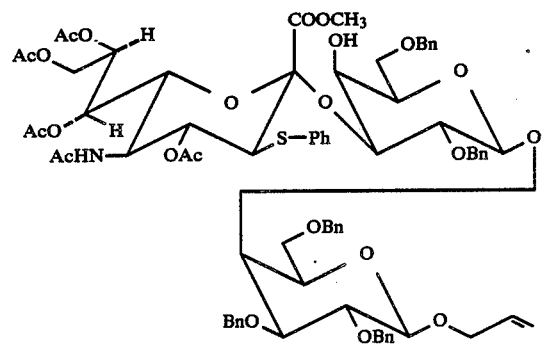

wherein Ac represents an acetyl group, Bn represents a benzyl group and Ph represents a phenyl group.

6. A sialic acid-containing oligosaccharide derivative represented by the formula (IV):

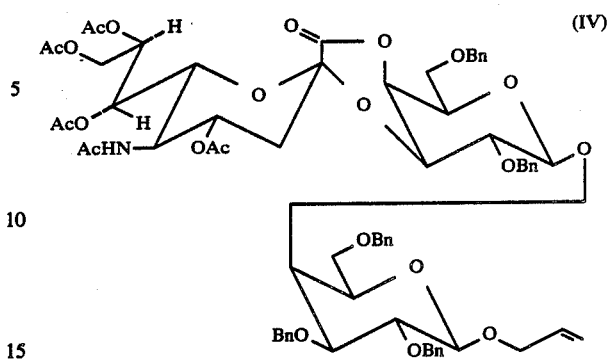

wherein Ac represents an acetyl group and Bn represents a benzyl group.

7. A process for preparing the sialic acid-containing oligosaccharide derivative represented by the formula (IV):

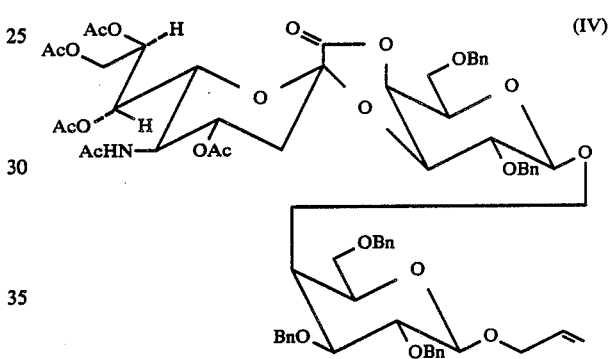

wherein Ac represents an acetyl group and Bn represents a benzyl group, which comprises reacting a dichloroethane mixed liquor containing the 3-phenylthiosialic acid derivative represented by the formula (Ia):

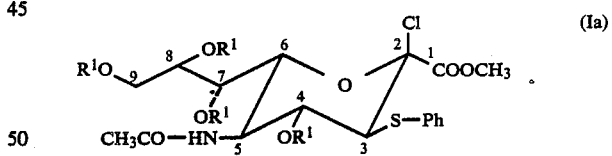

wherein R[1] represents an acetyl group, a benzyl group or a benzoyl group; and Ph represents a phenyl group, the compound represented by the formula (V):

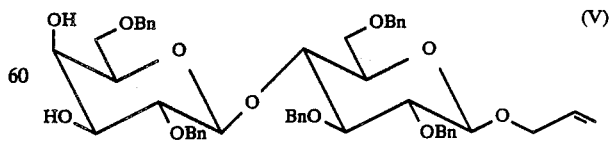

wherein Bn represents a benzyl group, molecular sieves and $Na_2HPO_4$ with a toluene solution containing silver trifluoracetate to obtain the sialic acid-containing oligosaccharide derivative represented by the formula (III):

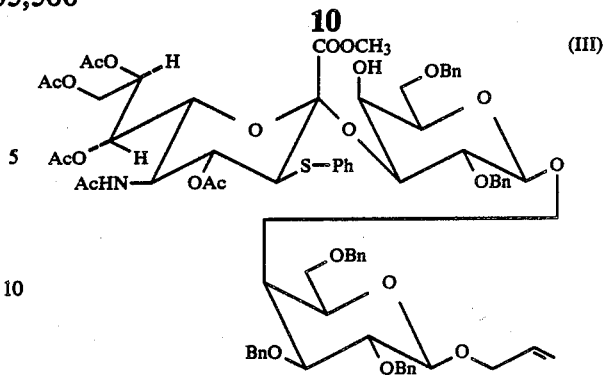

wherein Ac represents an acetyl group, Bn represents a benzyl group and Ph represents a phenyl group; and then reacting a toluene mixed liquor containing the sialic acid-containing oligosaccharide derivative represented by the formula (III) and α'-azobis-isobutyronitrile with (n-$C_4H_9$)$_3$SnH, to produce the sialic acid-containing oligosaccharide derivative represented by the formula (IV).

* * * * *